United States Patent [19]

Bertozzi et al.

[11] 4,285,826

[45] Aug. 25, 1981

[54] TOILET SOAP BARS IMPARTING IMPROVED MOISTURING AND SKIN FEEL CHARACTERISTICS

[75] Inventors: Richard J. Bertozzi; Joseph M. Pavelek, Jr.; Daniel S. Wood, all of Phoenix, Ariz.

[73] Assignee: Armour-Dial, Inc., Phoenix, Ariz.

[21] Appl. No.: 140,502

[22] Filed: Apr. 14, 1980

[51] Int. Cl.$^3$ .................. C11D 9/26; C11D 9/46
[52] U.S. Cl. .................. 252/117; 252/108; 252/132; 252/134; 252/174; 252/DIG. 16
[58] Field of Search .............. 252/108, 114, 117, 122, 252/132, 134, DIG. 26, 36

[56] References Cited

U.S. PATENT DOCUMENTS

| | | | |
|---|---|---|---|
| 2,543,744 | 3/1951 | Fox | 252/132 |
| 2,595,300 | 5/1952 | Safrin et al. | 252/109 |
| 2,774,735 | 12/1956 | Becher | 252/117 |
| 3,032,505 | 5/1962 | Glynn et al. | 252/122 |
| 3,312,627 | 4/1967 | Hooker | 252/547 |
| 3,598,746 | 8/1971 | Kaniecki et al. | 252/122 |
| 3,814,698 | 6/1974 | Ferrara et al. | 252/370 |
| 3,838,057 | 9/1974 | Barnes et al. | 252/117 |
| 4,148,743 | 4/1979 | Schubert | 252/132 |

FOREIGN PATENT DOCUMENTS

| | | | |
|---|---|---|---|
| 580206 | 7/1959 | Canada | 252/132 |
| 903781 | 8/1962 | United Kingdom . | |

*Primary Examiner*—P. E. Willis, Jr.
*Attorney, Agent, or Firm*—Frank T. Barber; Richard G. Harrer; Laird F. Miller

[57] ABSTRACT

This invention relates to toilet soap and more particularly to toilet soap which, when used, will reduce moisture loss from the skin and impart a refreshing skin feel.

11 Claims, No Drawings

TOILET SOAP BARS IMPARTING IMPROVED MOISTURING AND SKIN FEEL CHARACTERISTICS

BACKGROUND OF THE INVENTION

Skin dryness is a common affliction of mankind which has attracted a great deal of attention in the soap and cosmetic industries. Many approaches have been taken to combat this condition; for example, emollients have been applied which cause a physical soothing effect on the skin, but which provide only temporary relief. Other materials referred to as humectants have been applied which cause a transfer of water from deep in the skin or from the air to the upper layers of the skin. Still other materials have been applied which occlude the loss of water from the skin surface, and yet other materials which affect skin metabolism have been used. The most popular approach has been to use emollients which alleviate the symptoms of dryness by filling in the rough areas and indentations of the outer skin layer (the stratum corneum) to provide a lubricating effect; however, as noted above, in most instances the relief is only a temporary surface phenomenon which does not affect the physiological functions of the skin.

It is generally recognized that natural skin oils and water provide the moisturizing effect in skin; therefore, the state of hydration of the stratum corneum is of major importance. Several factors which influence the state of hydration have been suggested, including the rate at which water reaches the stratum corneum from lower layers of the skin, the ability of the stratum corneum to hold water, and the rate at which moisture evaporates from the skin. These factors all concern "transpirational" water; that is, water which migrates to the stratum corneum from the lower skin layers. Soaps and cosmetics can affect skin moisture. Consequently, measuring the transpirational water loss (TWL) from the stratum corneum is one way to evaluate the moisturizing ability of various soaps and cosmetic products.

The present invention concerns toilet soap which tends to reduce moisture loss from the skin and improve skin feel. Toilet soap is comprised primarily of water soluble ammonium, alkali metal or alkanolamine salts of various fatty acids having chiefly from 12 to 18 carbon atoms. Typical examples of such soap bases are lauric, oleic, stearic and palmitic acids which may be derived from various sources, including animal fat, vegetable fat, vegetable oil, fish oil and whale oil. The sodium and potassium salts of tallow and coco fats are preferred, with sodium tallow/sodium coco soaps in the proportions of generally 90-10 to 50—50 being especially desirable. Particularly preferred proportions of these two soap bases are 85/15 and 70/30.

Ordinary toilet soap, when applied to the skin, can cause irritation and dryness. To overcome these symptoms, various additives have been incorporated into soap bars. For example, certain lower molecular weight polyethylene glycols, when incorporated into creams and lotions, have been reported to promote improved skin feel. In U.S. Pat. No. 2,309,722, Wilkes et al. disclosed the use of polyethylene glycols having molecular weights of from about 400 to 4000 in creams, lotions and other toilet preparations to effect improved softening and conditioning of the skin. We have found that when polyethylene glycols having subtantially higher molecular weights (e.g., from 88,000 to ca. 4,000,000) are incorporated into soap bars, superior skin feel will initially result when the bars are used. However, this attribute is illusory for these materials also tend to cause an increased loss of transpirational water. As a result bars containing these materials eventually tend to induce skin dryness.

SUMMARY OF THE INVENTION

We have discovered that when soap is produced comprising about 60% to 95% anhydrous soap base as hereinbefore described, about 5 to 25% moisture, about 0.02% to 5% of a polyoxyethylene polymer of the formula

where n has an average value of from 2000 to 90000, and about 0.1% to 15% of a polymeric material selected from the group consisting of
(1) polypropoxylated materials of the formula

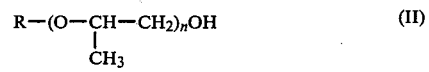

where
n has an average value of from 9 to 50, and
R is a hydrocarbon radical having from 3 to 6 carbon atoms,
(2) polypropoxylated materials of the formula

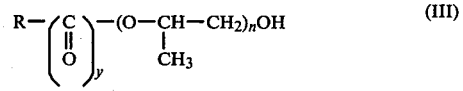

where
n has an average value of from 9 to 50,
R is a hydrocarbon radical having from 7 to 35 carbon atoms, and
y is 0 or 1,
(3) polyethoxylated materials of the formula

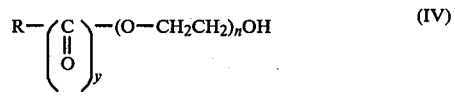

where
n has an average value of from 9 to 50,
R is a hydrocarbon radical having from 3 to 35 carbon atoms, and
y is 0 or 1, and
(4) mixtures thereof, the soap will reduce transpirational water loss and impart good skin feel. Thus, the combination retains the benefit obtained by adding various high molecular weight polyoxyethylenes to soap bars, yet overcomes the detrimental loss of transpirational water. Preferably, the levels of compounds of the type illustrated by formula (I) will range from 0.1% to 1.5%, and the levels of compounds of the type illustrated by formulas II, III, IV and mixtures thereof will range from 0.5% to 5%.

DETAILED DESCRIPTION OF PREFERRED EMBODIMENTS

Two compounds of choice to practice the present invention are PEG-5M, representing formula I, and PPG-14 butyl ether representing formula II. PEG-5M is the polymer of ethylene oxide which generally conforms to the formula $H(OCH_2CH_2)_nOH$ where n has an average value of 5000. This material and other compounds of this type are sold by Union Carbide Company under the name "Polyox"; thus PEG-5M is also known as Polyox WSR N-80. PPG-14 butyl ether is the polypropylene glycol ether of butyl alcohol that generally conforms to the formula $$C_4H_9(OCHCH_2)_nOH$$
$$|$$
$$CH_3$$

where n has an average value of 14. This material is sold by Union Carbide under the name Fluid AP. Other compounds of choice to practice the present invention are PEG-2M, PEG-7M and PEG-20M, all of which are representative of formula I where n has an average value of 2000, 7000 and 20,000, respectively; PPG-20 propyl ether and PPG-30 butyl ether, both of which are representative of formula II; PPG-30 isocetyl ether, PPG-11 stearyl ether, PPG-9 laurate and PPG-36 oleate, all of which are representative of formula III; and PEG-30 stearyl ether, PEG-20 stearate and PEG-20 oleate, all of which are representative of formula IV.

Soap bars comprising the present invention may be prepared in the following manner beginning with neat soap. The method in which soap is manufactured is discussed at length in *Encyclopedia of Chemical Technology* (2d Ed.) Vol. 18, pp. 415–432. Conventionally, fatty acids or esters thereof are saponified in a "kettle" process or, more preferably, by a continuous saponification process to yield a neat soap containing about 30% water. To practice the present invention, the polyoxyethylene polymer of formula I is added to the neat soap, after which the moisture level is reduced to 10–15% and the soap is pelletized. The pelletized soap is placed in an amalgamator and a mixture of perfume and one or more of the polymeric materials of formulas II–IV are added. In addition, an aqueous slurry containing other desirable ingredients may also be added at this point. Thereafter, the treated pellets are transferred to a plodder which screens the soap and extrudes it into a "log". Soap bars are then produced from the log by means well known in the art.

The advantages of using soap of the present invention may be seen from the following examples.

EXAMPLE 1

Soap bars having the compositions listed below were prepared and applied to nine test subjects, each test composition plus control being applied to a group of the three subjects.

| | Composition (Weight Percent) | | | |
|---|---|---|---|---|
| | Control | Control +PPG-14 butyl ether | Control +PEG-5M | Control +PPG-14 butyl ether +PEG-5M |
| 85/15 soap base (anhydrous) | 79.62 | 79.62 | 79.62 | 79.62 |
| Moisture | 17.73 | 16.88 | 16.88 | 16.88 |
| PPG-14 butyl ether | — | 0.85 | — | 0.75 |
| PEG-5M | — | — | 0.85 | 0.10 |
| Perfume and miscellaneous | 2.65 | 2.65 | 2.65 | 2.65 |

Each of the above compositions was examined by electrical hygrometry (EH) using the following procedure. Two test sites are selected on the forearm of a test panelist and the transpirational water loss (TWL) at each site is measured by placing a test chamber over the test site, passing an air stream of defined relative humidity and flow rate from the electrical hygrometer through the test chamber and back to the electrical hygrometer, and then measuring the humidity of the returning air. After the TWL values are measured for both untreated sites, one site is treated with test substance, the site is allowed to dry, and the TWL value of both sites is again determined. A TWL ratio is then determined for each site by dividing the second reading by the reading which was obtained first. For example, for the treated site, the reading following treatment is divided by the reading first obtained at that site prior to treatment.

To obtain the EH values as reported below, the TWL ratio for the treated site is divided by the TWL ratio for the untreated site. This serves to normalize the TWL ratio of the treated site and tends to eliminate error arising from normal physiological changes occurring in a panelist during the course of an experiment. The EH value is then defined as the TWL ratio of the treated site divided by the TWL ratio of the untreated site. The following average EH values were recorded.

| | Control | Control +PPG-14 butyl ether | Control +PEG-5M | Control +PPG-14 butyl ether +PEG-5M |
|---|---|---|---|---|
| EH values | 1.18 ± 0.10 | 1.14 ± 0.14 | 1.22 ± 0.23 | 1.13 ± 0.06 |

If an EH value for a substance is 1.0, no change in TWL has occurred in the treated site as compared to the untreated site. If the EH value is greater than 1.0, the TWL of the treated site is greater than the TWL of the untreated site. Accordingly, the above values indicate that, as compared to control, a soap bar containing only PPG-14 butyl ether causes a reduction in transpirational water loss, a soap bar containing only PEG-5M causes an increase in transpirational water loss, and a soap bar containing a combination of the two additives causes a reduction in transpirational water loss comparable to that caused by the bar containing only PPG-14 butyl ether.

EXAMPLE 2

A similar result was obtained for a larger scale study using twenty-five test subjects. Control bars having essentially the same composition as the control illustrated for Example 1 were compared with test bars containing both PPG-14 butyl ether and PEG-5M at the levels set forth above. The following EH values were recorded.

| | Control | Control +PPG-14 butyl ether +PEG-5M |
|---|---|---|
| EH values | 1.164 | 1.032 |

As in Example 1, the bars containing PPG-14 butyl ether and PEG-5M showed a substantial reduction in transpirational water loss versus control.

EXAMPLE 3

Various skin feel characteristics were measured by consumer panels. Two consumer panels, each containing 275 individuals, were selected and the panelists were given questionnaires and one of two types of test bars for use at home. All test bars were formulated with both PPG-14 butyl ether and PEG-5M, essentially as described in Example 1; however, one bar contained 85/15 soap base whereas the other contained 70/30 soap base. Panelists were asked to rate the bars after their first use and after their last use. In both instances, a bipolar attribute scale was used, with 1 being the worst rating and 10 being the best rating.

| Test Bars Containing PPG-14 butyl ether and PEG-5M | | |
|---|---|---|
| Attribute | 70/30 base | 85/15 base |
| Soap is mild and gentle | 8.01 | 8.06 |
| Does not leave skin feeling dry | 8.48 | 8.43 |
| Makes skin feel smooth | 8.34 | 8.21 |
| Leaves skin feeling clean | 8.65 | 8.47 |
| Lather feels nice on skin | 8.35 | 8.26 |
| Makes skin feel good | 8.48 | 8.29 |
| Not irritating to skin | 8.09 | 8.05 |

As seen from the data, comparable favorable results were obtained regardless of the soap base used.

Our invention is not restricted solely to the descriptions and illustrations provided above, but encompasses all modifications envisaged by the following claims:

We claim:

1. A toilet soap which, when applied to the skin, reduces transpirational water loss and imparts a good skin feel, said soap comprising
   (a) from about 60% to 95% by weight of an anhydrous soap base composition consisting essentially of salts of fatty acids having from 12 to 18 carbon atoms, said salts being selected from the group consisting of alkali metal, ammonium or alkanolamine;
   (b) from about 5% to 25% moisture;
   (c) from about 0.02% to 5% of a polyoxyethylene polymer of the formula H $(OCH_2CH_2)_n$ OH where n has an average value from 2000 to 90,000; and
   (d) from about 0.1% to 15% of a polymeric material selected from the group consisting of
   (1) polypropoxylated materials of the formula

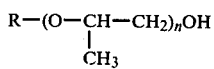

where
   n has an average value of from 9 to 50, and
   R is a hydrocarbon radical having from 3 to 6 carbon atoms,
   (2) polypropoxylated materials of the formula

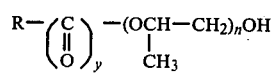

where
   n has an average value of from 9 to 50,
   R is a hydrocarbon radical having from 7 to 35 carbon atoms, and
   y is 0 or 1, (3) polyethoxylated materials of the formula

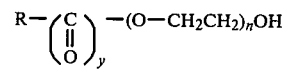

where
   n has an average value from of 9 to 50,
   R is a hydrocarbon radical having from 3 to 35 carbon atoms, and
   y is 0 or 1, and
   (4) mixtures thereof, 2. A toilet soap according to claim 1 wherein said soap comprises from about 0.1% to 1.5% of said polyoxyethylene polymer and from about 0.5% to 5% of said polymeric materials.

3. A toilet soap according to claim 2 wherein "n" of said polyoxyethylene polymer is 2000.

4. A toilet soap according to claim 2 wherein "n" of said polyoxyethylene polymer is 5000.

5. A toilet soap according to claim 2 wherein "n" of said polyoxyethylene polymer is 7000.

6. A toilet soap according to claim 2 wherein "n" of said polyoxyethylene polymer is 20,000.

7. A toilet soap according to claim 2 wherein said polymeric material is

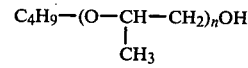

where
n has an average value of 14.

8. A toilet soap according to claim 2 wherein said polymeric material is

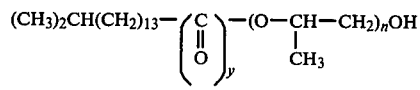

where
n has an average value 30, and
y is 0.

9. A toilet soap according to claim 2 wherein said polymeric material is

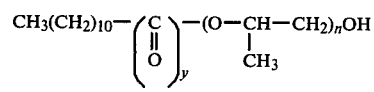

where
n has an average value of 9 and
y is 1.

10. A toilet soap according to claim 2 wherein said polymeric material is

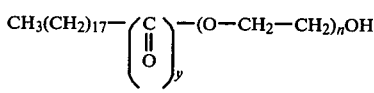

where
n has an average of 30, and
y is 0.

11. A toilet soap according to claim 2 wherein said polymeric material is

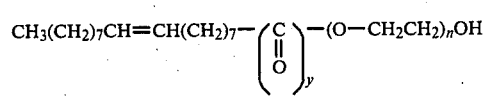
where
n has an average value of 20, and
y is 1.
* * * * *